United States Patent [19]

Rausch

[11] 4,013,733

[45] * Mar. 22, 1977

[54] DEHYDROGENATION METHOD

[75] Inventor: Richard E. Rausch, Mundelein, Ill.

[73] Assignee: UOP Inc., Des Plaines, Ill.

[ * ] Notice: The portion of the term of this patent subsequent to Feb. 17, 1993, has been disclaimed.

[22] Filed: Oct. 6, 1975

[21] Appl. No.: 620,078

Related U.S. Application Data

[60] Division of Ser. No. 434,476, Jan. 18, 1974, Pat. No. 3,939,220, which is a continuation-in-part of Ser. No. 304,177, Nov. 6, 1972, Pat. No. 3,790,473, which is a continuation-in-part of Ser. No. 142,079, May 10, 1971, Pat. No. 3,702,294, which is a continuation-in-part of Ser. Nos. 819,114, April 24, 1969, abandoned, and Ser. No. 807,910, March 17, 1969, Pat. No. 3,740,328.

[52] U.S. Cl. .................. 260/668 D; 208/138; 260/669 R; 260/683.3

[51] Int. Cl.$^2$ .................. C10G 35/06; C07C 3/28; C07C 5/32

[58] Field of Search ........... 208/138, 668 D, 683.3, 208/669 R

[56] References Cited

UNITED STATES PATENTS

| | | | |
|---|---|---|---|
| 2,861,959 | 11/1958 | Thorn et al. | 208/138 |
| 2,952,611 | 9/1960 | Haxton et al. | 208/65 |
| 3,415,737 | 12/1968 | Kluksdahl | 208/138 |
| 3,449,237 | 6/1969 | Jacobson et al. | 208/138 |
| 3,578,583 | 5/1971 | Buss | 208/138 |
| 3,631,215 | 12/1971 | Clippinger et al. | 208/138 |
| 3,790,473 | 2/1974 | Rausch | 208/139 |
| 3,939,220 | 2/1976 | Rausch | 208/138 |

*Primary Examiner*—Delbert E. Gantz
*Assistant Examiner*—James W. Hellwege
*Attorney, Agent, or Firm*—James R. Hoatson, Jr.; Thomas K. McBride; William H. Page, II

[57] ABSTRACT

Dehydrogenatable hydrocarbons are dehydrogenated by contacting them at dehydrogenation conditions with a catalytic composite, comprising a combination of catalytically effective amounts of a platinum or palladium component, an iridium component, a rhenium component, and a tin component with a porous carrier material. A specific example of the subject dehydrogenation method involves contacting a dehydrogenatable hydrocarbon and hydrogen, at dehydrogenation conditions, with a catalytic composite comprising a combination of a platinum or palladium component, an iridium component, a rhenium component, and a tin component with a porous carrier material wherein substantially all of the platinum or palladium component, the iridium component and the rhenium component are present as the corresponding elemental metals and substantially all of the tin component is present in an oxidation state above the elemental metal, and wherein the composite contains about 0.01 to about 2 wt.% platinum or palladium, about 0.01 to about 2 wt.% iridium, about 0.01 to about 2 wt.% rhenium, and about 0.01 to about 5 wt.% tin.

12 Claims, No Drawings

DEHYDROGENATION METHOD

CROSS-REFERENCES TO RELATED APPLICATIONS

This application is a Division of my copending application Ser. No. 434,476 filed Jan. 18, 1974 now U.S. Patent 3,939,220; which in turn is a Continuation-In-Part of my prior application Serial No. 304,177 filed Nov. 6, 1972 and now U.S. Patent No. 3,790,473; which in turn is a Continuation-In-Part of my prior application Serial No. 142,079 filed May 10, 1971 and now U.S. Patent No. 3,702,294; and which in turn is a Continuation-In-Part of my prior, now abandoned application Serial No. 819,114 filed Apr. 24, 1969 and of my prior application Serial No. 807,910 filed Mar. 17, 1969 and now U.S. Patent No. 3,740,328. All of the teachings of these prior applications are specifically incorporated herein by reference.

The subject of the present invention is, broadly, an improved method for dehydrogenating a dehydrogenatable hydrocarbon to produce a hydrocarbon product containing the same number of carbon atoms but fewer hydrogen atoms. In another aspect, the present invention involves a method of dehydrogenating normal paraffin hydrocarbons containing 4 to 30 carbon atoms per molecule to the corresponding normal mono-olefin with minimum production of side products. In yet another aspect, the present relates to a novel multimetallic catalytic composite comprising a combination of catalytically effective amounts of a platinum or palladium component, an iridium component, a rhenium component, a tin component, and an alkali or alkaline earth component with a porous carrier material, which composite has highly beneficial characteristics of activity, selectivity and stability when it is employed in the dehydrogenation of dehydrogenatable hydrocarbons such as aliphatic hydrocarbons, naphthene hydrocarbons and alkylaromatic hydrocarbons.

The conception of the present information followed from my search for a novel catalytic composite processing a hydrogenation-dehydrogenation function, a controllable cracking function, and superior conversion, selectivity and stability characteristics when employed in hydrocarbon conversion processes that have traditionally utilized dual-function catalytic composites. In my prior applications, I disclosed a significant finding with respect to a tetrametallic catalytic composite meeting these requirements. More specifically, I determined that a combination of iridium, rhenium and tin be utilized, under certain conditions, to beneficially interact with the platinum or palladium component of a dual-function catalyst with a resulting marked improvement in the performance of such a catalyst. Now I have ascertained that a catalytic composite, comprising a combination of catalytically effective amounts of a platinum or palladium component, an iridium component, a rhenium component and a tin component with a porous carrier material can have superior activity, selectivity and stability characteristics when it is employed in a dehydrogenation process if the oxidation state of the metallic ingredients are carefully controlled so that substantially all of the platinum or palladium, the iridium and the rhenium components are present as the corresponding elemental metals and substantially all of the tin component is present in an oxidation state above that of the elemental metal. Moreover, I have discerned that a particularly preferred multimetallic catalytic composite of this type contains not only a platinum or palladium component, an iridium component, a rhenium component, and a tin component, but also an alkali or alkaline earth component.

The dehydrogenation of dehydrogenatable hydrocarbons is an important commercial process because of the great and expanding demand for dehydrogenated hydrocarbons for use in the manufacture of various chemical products such as detergents, plastics, synthetic rubbers, pharmaceutical products, high octane gasoline, perfumes, drying oils, ion-exchange resins, and various other products well known to those skilled in the art. One example of this demand is in the manufacture of high octane gasoline by using $C_3$ and $C_4$ mono-olefins to alkylate isobutane. Another example of this demand is in the area of dehydrogenation of normal paraffin hydrocarbons to produce normal mono-olefins having 4 to 30 carbon atoms per molecule. These normal mono-olefins can, in turn, be utilized in the synthesis of a vast number of other chemical products. For example, derivatives of normal mono-olefins have become of substantial importance to the detergent industry where they are utilized to alkylate an aromatic, such as benzene, with subsequent transformation of the product arylalkane into a wide variety of biodegradable detergents such as the alkylaryl sulfonate type of detergent which is most widely used today for household, industrial, and commercial purposes. Still another large class of detergents produced from these normal mono-olefins are the oxyalkylated phenol derivatives in which the alkyl phenol base is prepared by the alkylation of phenol with these normal mono-olefins. Still another type of detergents produced from these normal mono-olefins are the biodegradable alkylsulfates formed by the direct sulfation of the normal mono-olefins. Likewise, the olefin can be subjected to direct sulfonation with sodium bisulfite to make biodegradable alkylsulfonates. As a further example, these mono-olefins can be hydrated to produce alcohols which then, in turn, can be used to produce plasticizers and/or synthetic lube oils.

Regarding the use of products made by the dehydrogenation of alkylaromatic hydrocarbons, they find wide application in industries including the petroleum, petrochemical, pharmaceutical, detergent, plastic industries, and the like. For example, ethylbenzene is dehydrogenated to produce styrene which is utilized in the manufacture of polystyrene plastics, styrene-butadiene rubber, and the like products. Isopropylbenzene is dehydrogenated to form alpha-methylstyrene which, in turn, is extensively used in polymer formation and in the manufacture of drying oils, ion exchange resins, and the like materials.

Responsive to this demand for these dehydrogenation products, the art has developed a number of alternative methods to produce them in commercial quantities. One method that is widely utilized involves the selective dehydrogenation of a dehydrogenatable hydrocarbon by contacting the hydrocarbon with a suitable catalyst at dehydrogenation conditions. As is the case with most catalytic procedures, the principal measure of effectiveness for this dehydrogenation method involves the ability to perform its intended function with minimum interference of side reactions for extended periods of time. The analytical terms used in the art to broadly measure how well a particular catalyst performs its intended functions in a particular hydrocarbon conversion reaction are activity, selectivity and stability, and for purposes of discussion here these terms are generally defined for a given reactant as follows: (1) activity is a measure of the catalyst's ability to convert the hydrocarbon reactant into products at a specified severity level where severity level means the specific reaction conditions used — that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters—obviously the smaller rate implying the more stable catalyst. More specifically, in a dehydrogenation process, activity commonly refers to the amount of conversion that takes place for a given dehydrogenatable hydrocarbon at a specified severity level and is typically measured on the basis of disappearance of the dehydrogenatable hydrocarbon; selectivity is typically measured by the amount, calculated on a mole percent of converted dehydrogenatable hydrocarbon basis, of the desired dehydrogenated hydrocarbon obtained at the particular severity level; and stability is typically equated to the rate of change with time of activity as measured by disappearance of the dehydrogenatable hydrocarbon and of selectivity as measured by the amount of desired hydrocarbon produced. Accordingly, the major problem facing workers in the hydrocarbon dehydrogenation art is the development of a more active and selective catalytic composite that has good stability characteristics.

I have now found a catalytic composite which possesses improved activity, selectivity, and stability when it is employed in a process for the dehydrogenation of dehydrogenatable hydrocarbons. In particular, I have determined that a combination of catalytically effective amounts of a platinum or palladium component, an iridium component, a rhenium component and a tin component with a porous, refractory carrier material can enable the performance of a dehydrogenation process to be substantially improved. Moreover, particularly good results are obtained when this composite is combined with an alkali or alkaline earth component and utilized to produce dehydrogenated hydrocarbons containing the same carbon structure as the rectant hydrocarbon but fewer hydrogen atoms. This last composite is particularly useful in the dehydrogenation of long chain normal paraffins to produce the corresponding normal mono-olefin with minimization of side reactions such as skeletal isomerization, aromatization, and cracking.

It is, accordingly, one object of the present invention to provide a novel method for the dehydrogenation of dehydrogenatable hydrocarbons utilizing a multimetallic catalytic composite comprising a platinum or palladium component, an iridium component, a rhenium component and a tin component combined with a porous carrier material. A second object is to provide a novel nonacidic catalytic composite having superior performance characteristics when utilized in a dehydrogenation process. Another object is to provide an improved method for the dehydrogenation of normal paraffin hydrocarbons to produce normal mono-olefins which method minimizes undesirable side reactions such as cracking, skeletal isomerization and aromatization.

In brief summary, one embodiment of the present invention involves a method for dehydrogenating a dehydrogenatable hydrocarbon which comprises contacting the hydrocarbon with a multimetallic catalytic composite, containing a platinum or palladium component, an iridium component, a rhenium component and a tin component combined with a porous carrier material, at dehydrogenation conditions. Moreover, substantially all of the platinum or palladium, iridium and rhenium are present in the composite as the corresponding elemental metals and substantially all of the tin component is present in an oxidation state above that of the elemental metal. Further, these components are present in this composite in amounts, calculated on an elemental basis, sufficient to result in the composite containing about 0.01 to about 2 wt. % platinum or palladium, about 0.01 to about 2 wt. % iridium, about 0.01 to about 2 wt. % rhenium and about 0.01 to about 5 wt. % tin.

A second embodiment relates to the dehydrogenation method described in the first embodiment wherein the dehydrogenatable hydrocarbon is an aliphatic compound containing 2 to 30 carbon atoms per molecule.

A third embodiment comprehends a catalytic composite comprising a combination of a platinum or palladium component, an iridium component, a rhenium component, a tin component, and an alkali or alkaline earth component with a porous carrier material. These components are furthermore present in amounts sufficient to result in the catalytic composite containing, on an elemental basis, about 0.01 to about 2 wt. % platinum or palladium, about 0.01 to about 5 wt. % of the alkali metal or alkaline earth metal, about 0.01 to about 2 wt. % iridium, about 0.01 to about 2 wt. % rhenium and about 0.01 to about 5 wt. % tin. In addition, substantially all of the platinum or palladium, iridium, and rhenium components are present as the corresponding elemental metals and substantially all of the tin component is present in an oxidation state above that of the elemental metal.

Another embodiment pertains to a method for dehydrogenating a dehydrogenatable hydrocarbon which comprises contacting the hydrocarbon with the catalytic composite described in the third embodiment at dehydrogenation conditions.

Other object and embodiments of the present invention involve specific details regarding essential and preferred catalytic ingredients, preferred amounts of ingredients, suitable methods of multimettalic composite preparation, suitable dehydrogenatable hydrocarbons, operating conditions for use in the dehydrogenation process, and the like particulars. These are hereinafter given in the following detailed discussion of each of these facets of the present invention.

Regarding the dehydrogenatable hydrocarbon that is subjected to the method of the present invention, it can, in general, may be organic compound having 2 to 30 carbon atoms per molecule and containing at least 1 pair of adjacent carbon atoms having hydrogen attached thereto. That is, it is intended to include within the scope of the present invention, the dehydrogenation of any organic compound capable of being dehydrogenated to produce products containing the same number of carbon atoms but fewer hydrogen atoms, and capable of being vaporized at the dehydrogenation temperatures used herein. More particularly, suitable dehydrogenatable hydrocarbons are: aliphatic compounds containing 2 to 30 carbon atoms per molecule, alkylaromatic hydrocarbons where the alkyl group contains 2 to 6 carbon atoms, and naphthenes or alkyl-substituted naphthenes. Specific examples of suitable dehydrogenatable hydrocarbons are: (1) alkanes such as ethanes, propane, n-butane, isobutane, n-pentane, isopentane, n-hexane, 2-methylhexane, 2-methylpentane, 2,2-dimethylbutane, n-heptane, 2-methylhexane, 2,2,3-trimethylbutane, and the like compounds; (2) naphthenes such as cyclopentane, cyclohexane, methylcyclopentane, ethylcyclopentane, n-propylcyclopentane, 1,3-dimethylcyclohexane, and the like compounds; and (3) alkylaromatics such as ethylbenzene, n-butylbenzene, 1,3,5-triethylbenzene, isopropylbenzene, isobutylbenzene, ethylnaphthalene, and the like compounds.

In a preferred embodiment, the dehydrogenatable hydrocarbon is a normal paraffin hydrocarbon having about 4 to about 30 carbon atoms per molecule. For example, normal paraffin hydrocarbons containing about 10 to 18 carbon atoms per molecule are dehydrogenated by the subject method to produce the corresponding normal mono-olefin which can, in turn, be alkylated with benzene and sulfonated to make alkylbenzene sulfonate detergents having superior biodegradibility. Likewise, n-alkanes having 10 to 18 carbon atoms per molecule can be dehydrogenated to the corresponding normal mono-olefin which, in turn, can be sulfonated or sulfated to make excellent detergents. Similarly, n-alkanes having 6 to 10 carbon atoms can be dehydrogenated to form the corresponding mono-olefin which can, in turn, be hydrated to produce valuable alcohols. Preferred feed streams for the manufacture of detergent intermediates contain a mixture of 4 or 5 adjacent normal paraffin homologues such as $C_{10}$ to $C_{13}$, $C_{11}$ to $C_{14}$, $C_{11}$ to $C_{15}$, and the like mixtures.

The multimetallic catalyst of the present invention comprises a porous carrier material or support having combined therewith catalytically effective amounts of a platinum or palladium component, and iridium component, a rhenium component, a tin component and in the preferred case, an alkali or alkaline earth component. Considering first the porous carrier material utilized in the present invention, it is preferred that the material be a porous, adsorptive, high-surface area support having a surface area of about 25 to about 500 $m^2/g$. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically prepared and naturally-occurring, which may or may not be acid treated, for example, attapulgus clay, china clay, diatomaceous earth, fuller's earth, kaoline, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromiaalumina, alumina-boria, silica-zirconia, etc.; (5) crystalline zeolitic aluminosilicates such as naturally-occurring or synthetically-prepared mordenite and/or faujasite, either in the hydrogen form or in a form which has been treated with multi-valent cations; (6) spinels such as $MgAl_2O_4$, $FeAl_2O_4$, $ZnAl_2O_4$, $MnAl_2O_4$, $CaAl_2O_4$ and other like compounds having the formula $MO \cdot Al_2O_3$ where M is a metal having a valence of 2; and (7) combinations of elements from one or more of these groups. The preferred porous carrier material for use in the present invention are refracory inorganic oxides, with best results obtained with an alumina carrier material. Suitable alumina materials are the crystalline aluminas known as the gammas-, eta-, and thetaalumina, with gamma- or eta-alumina giving best results. In addition, in some embodiments the alumina carrier material may contain minor proportions of other well-known refractory inorganic oxides such as silica, zirconia, magnesia, etc.; however, the preferred support is substantially pure gamma- or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 $m^2/g$. In general, best results are typically obtained with a gamma-alumina carrier material which is used in the form of spherical particles having: a relatively small diameter (i.e. typically about 1/16 inch), an apparent bulk density of about 0.5 to about 0.6 g/cc, a pore volume of about 0.4 cc/g, and a surface area of about 175 $m^2/g$.

The preferred alumina carrier material may be prepared in any suitable manner and may be synthetically prepared or natural occurring. Whatever type of alumina is employed it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, etc., and utilized in any desired size. For the purpose of the present invention a particularly preferred form of alumina is the sphere; and alumina spheres may be continuously manufactured by the well-known oil drop method which comprises; forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

One essential constituent of the multimetallic catalyst of the present invention is a tin component. It is an essential feature of the present invention that the tin component is present in the multimetallic composite in an oxidation state above that of the elemental metal. That is, the tin component will exist in the present catalytic composite in either the +2 or +4 oxidation state with the latter being the most likely state. Accordingly, the tin component will be present in the composite as a chemical compound, such as the oxide, sulfide, halide, etc., wherein the tin moiety is in the required oxidation state, or as a chemical combination with the carrier material in which combination the tin moiety exists in this higher oxidation state. On the basis of the evidence currently available, it is believed that the tin component in the subject composite exists in the form of tin oxide — that is, as stannic or stannous oxide. It is important to note that this limitation on the state of the tin component requires extreme care in the preparation and use of the subject composite in order to insure that it is subjected to oxidation conditions effective to produce tin oxide and that it is not thereafter subjected to high temperature reduction conditions effective to produce the tin metal. Preferably, the tin component is used in an amount sufficient to result in the final catalytic composite containing, on an elemental basis, about 0.01 to about 5 wt. % tin, with best results typically obtained with about 0.1 to about 2 wt. % tin.

This tin component may be incorporated in the multimetallic catalytic composite in any suitable manner known to result in a relatively uniform distribution of the tin moiety in the carrier material, such as by coprecipitation or cogellation with the porous carrier material, ion exchange with the carrier material or impregnation of the carrier material at any stage in the preparation. It is to be noted that it is intended to include within the scope of the present invention all conventional methods for incorporating a uniform distribution of the metallic component in a catalytic composite, and the particular method of incorporation used is not deemed to be an essential feature of the present invention. One preferred method of incorporating the tin component into the catalytic composite involves coprecipitating the tin component during the preparation of the preferred refractory oxide carrier material. In the preferred case, this involves the addition of suitable soluble tin compounds such as stannous or stannic halide to the alumina hydrosol, and then combining the hydrosol with a suitable gelling agent, and dropping the resulting mixture into an oil bath, etc., as explained in detail hereinbefore. Following the calcination step, there is obtained a carrier material comprising an intimate combination of alumina and stannic oxide. Another preferred method of incorporating the tin component into the catalytic composite involves the utilization of a soluble, decomposable compound of tin to impregnate the porous carrier material. Thus, the tin component may be added to the carrier material by commingling the latter with an aqueous solution of a suitable tin salt or water-soluble compound of tin such as stannous bromide, stannous chloride, stannic chloride, stannic chloride pentahydrate, stannic chloride tetrahydrate, stannic chloride trihydrate, stannic chloride diamine, stannic trichloride bromide, stannic chromate, stannous fluoride, stannic fluoride, stannic iodide, stannic sulfate, stannic tartrate, and the like compounds. The utilization of a tin chloride compound, such as stannous or stannic chloride is particularly preferred. In general, the tin component can be impregnated either prior to, simultaneously with, or after the other metallic components are added to the carrier material. However, I have found that excellent results are obtained when the tin component is impregnated simultaneously with the other metallic components. In fact, a preferred impregnation solution contains chloroplatinic acid, perrhenic acid, chloroiridic acid, stannous or stannic chloride and a strong acid such as hydrochloric acid, nitric acid and the like.

Regardless of which tin compound is used in the preferred impregnation step, it is extremely important that the tin component be uniformly distributed throughout the carrier material during this step. In order to achieve this objective it is necessary to maintain the pH of the impregnation solution in at a relatively low level, a range of about 1 to about 7, preferably 1 to about 3, and to dilute the impregnation solution to a volume which is approximately equivalent to or greater than the volume of the carrier material which is impregnated. It is preferred to use a volume ratio of impregnation solution to carrier material of at least 0.5:1 and preferably about 0.75:1 to about 2:1 or more. Similarly, it is preferred to use a relatively long contact time during the impregnation step ranging from about ¼ hour up to about ½ hour or more before drying to remove excess solvent in order to insure a high dispersion of the tin component into the carrier material. The carrier material is, likewise, preferably constantly agitated during this preferred impregnation step.

A second essential ingredient of the subject multimetallic catalyst is the platinum or palladium component. That is, it is intended to cover the use of platinum or palladium or mixtures thereof as a second component of the present composite. It is an essential feature of the present invention that substantially all of this platinum or palladium components exists within the final catalytic composite in the elemental metallic state. Generally, the amount of this component present in the final catalyst composite is small compared to the quantities of the other components combined therewith. In fact, the platinum or palladium component generally will comprise about 0.01 to about 2 wt. % of the final catalytic composite, calculated on an elemental basis. Excellent results are obtained when the catalyst contains about 0.05 to about 1 wt. % of the platinum or palladium metal.

This platinum or palladium component may be incorporated in the catalytic composite in any suitable manner known to result in a relatively uniform distribution of this component in the carrier material such as coprecipitation or cogellation, ion-exchange, or impregnation. The preferred method of preparing the catalyst involves the utilization of a soluble, decomposable compound of platinum or palladium to impregnate the carrier material in a relatively uniform manner. For example, this component may be added to the support by commingling the latter with an aqueous solution of chloroplatinic or chloropalladic acid. Other water-soluble compounds of platinum or palladium may be employed in impregnation solutions and include ammonium chloroplatinate, bromoplatinic acid, platinum dichloride, platinum tetrachloride hydrate, platinum dichlorocarbonyl dichloride, dinitrodiaminoplatinum, palladium chloride, palladium nitrate, palladium sulfate, etc. The utilization of a platinum or palladium chloride compound, such as chloroplatinic or chloropalladic acid, is generally preferred. Hydrogen chloride, nitric acid or the like acid is also generally added to the impregnation solution in order to further facilitate the uniform distribution of the metallic component throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

Yet another essential ingredient of the present multimetallic catalytic composite is an iridium component. It is of fundamental importance that substantially all of the iridium component exists within the catalytic composite of the present invention in the elemental metallic state and the subsequently described reduction procedure is designed to accomplish this objective. The iridium component may be utilized in the composite in any amount which is catalytically effective, with the preferred amount being about 0.01 to about 2 wt. % thereof, calculated on an elemental iridium basis. Typically best results are obtained with about 0.05 to about 1 wt. % iridium. It is, additionally, preferred to select the specific amount of iridium from within this broad weight range as a function of the amount of the platinum or palladium component, on an atomic basis, as is explained hereinafter.

This iridium component may be incorporated into the catalytic composite in any suitable manner known to those skilled in the catalyst formulation art which results in a relatively uniform dispersion of iridium in the carrier material. In addition, it may be added at any stage of the preparation of the composite — either during preparation of the carrier material or thereafter — and the precise method of incorporation used is not deemed to be critical. However, best results are thought to be obtained when the iridium component is relatively uniformly distributed throughout the carrier material, and the preferred procedures are the ones known to result in a composite having this relatively uniform distribution. One acceptable procedure for incorporating this component into the composite involves cogelling or coprecipitating the iridium component during the preparation of the preferred carrier material, alumina. This procedure usually comprehends the addition of a soluble, decomposable compound of iridium such as iridium tetrachloride to the alumina hydrosol before it is gelled. The resulting mixture is then finished by conventional gelling, aging, drying and calcination steps as explained hereinbefore. A preferred way of incorporating this component is an impregnation step wherein the porous carrier material is impregnated with a suitable iridium-containing solution either before, during or after the carrier material is calcined. Preferred impregnation solutions are aqueous solutions of water soluble, decomposable iridium compounds such as iridium tribromide, iridium dichloride, iridium tetrachloride, iridium oxalic acid, iridium sulfate, potassium iridochloride, chloroiridic acid, hexamine iridium chloride, and the like compounds. Best results are ordinarily obtained when the impregnation solution is an aqueous solution of chloroiridic acid or sodium chloroiridate. This component can be added to the carrier material, either prior to, simultaneously with or after the other metallic components are combined therewith. Best results are usually achieved when this component is added simultaneously with the other metallic components. In fact, excellent results are obtained with a one step impregnation procedure using an aqueous solution comprising chloroplatinic or chloropalladic acid, chloroiridic acid, and a strong acid such as hydrochloric acid, nitric acid, etc.

Yet another essential component of the catalyst of the present invention is the rhenium component. It is an essential feature of the present invention that substantially all of the rhenium component of the catalyst is present therein as the elemental metal, and the hereinafter described reduction step is specifically designed to reduce this component along with the platinum or palladium component and the iridium component to the corresponding metallic states. The rhenium component is preferably utilized in an amount sufficient to result in a final catalytic composite containing about 0.01 to about 2 wt. % rhenium and preferably about 0.05 to about 1, calculated on an elemental basis.

The rhenium component may be incorporated in the catalytic composite in any suitable manner and at any stage in the preparation of the catalyst. It is generally advisable to incorporate the rhenium component in an impregnation step after the porous carrier material has been formed in order tat the expensive metal will not be lost due to washing and purification treatments which may be applied to the carrier material during the course of its production. Although any suitable method for incorporating a catalytic component in a porous carrier material can be utilized to incorporate the rhenium component, the preferred procedure involves impregnation of the porous carrier material. The impregnation solution can, in general, be a solution of a suitable soluble, decomposable rhenium salt such as ammonium perrhenate, sodium perrhenate, potassium perrhenate, and the like salts. In addition, solutions of rhenium halides such as rhenium chloride may be used; the preferred impregnation solution is, however, an aqueous solution of perrhenic acid. The porous carrier material can be impregnated with the rhenium component either prior to, simultaneously with, or after the other components mentioned herein are combined therewith. Best results are ordinarily achieved when the rhenium component is impregnated simultaneously with the platinum or palladium, cin and iridium components. In fact, excellent results are obtained with a one step impregnation procedure utilizing as an impregnation solution, an aqueous solution of chloroplatinic acid, chloroiridic acid, perrhenic acid, stannic chloride, and a strong acid such as hydrochloric acid, nitric acid and the like.

Regarding the preferred amounts of te various metallic components of the subject catalyst, I have found it to be a good practice to specify the amounts of the iridium component, the rhenium component, and the tin component as a function of the amount of the platinum or palladium component. On this basis, the amount of the rhenium component is ordinarily selected so that the atomic ratio of rhenium to platinum or palladium metal contained in the composite is about 0.1:1 to about 3:1, with the preferred range being about 0.25:1 to about 1.5:1. Similarly, the amount of the tin component is ordinarily selected to produce a composite containing an atomic ratio of tin to platinum or palladium metal of about 0.1:1 to about 3:1, with the preferred range being about 0.25:1 to about 2:1. In the same manner, the amount of the iridium component is preferably selected so that the atomic ratio of iridium to platinum or palladium is about 0.1:1 to about 2:1.

Another significant parameter of the instant catalyst is the "total metals content" which is defined to be the sum of the platinum or palladium component, the iridium component, the rhenium component, and the tin component, calculated on an elemental tin, rhenium, iridium and platinum or palladium metal basis. Good results are ordinarily obtained with the subject catalyst when this parameter is fixed at a value of about 0.15 to about 5 wt. %, with best results ordinarily achieved at a metals loading of about 0.3 to about 2 wt. %.

Integrating the above discussion of each of the essential components of the multimetallic catalytic composite, it is evident that a particularly preferred catalytic composite comprises a combination of a platinum component, an iridium component, a rhenium component and a tin component with an alumina carrier material in amounts sufficient to result in the composite containing about 0.05 to about 1 wt. % platinum, about 0.05 to about 1 wt. % iridium, about 0.05 to about 1 wt. % rhenium, and about 0.05 to about 2 wt. % tin. Accordingly, specific examples of especially preferred catalytic composite are as follows: (1) a catalytic composite comprising a combination of 0.5 wt. % tin, 0.5 wt. % rhenium, 0.5 wt. % iridium and 0.75 wt. % platinum with an alumina carrier material; (2) a catalytic composite comprising a combination of 0.1 wt. % tin, 0.1 wt. % rhenium, 0.1 wt. % iridium and 0.1 wt. % platinum with an alumina carrier material; (3) a catalytic composite comprising a combination of about 0.375 wt. % tin, 0.375 wt. % rhenium, 0.375 wt. % platinum and 0.375 wt. % iridium with an alumina carrier material; (4) a catalytic composite comprising a combination of 0.12 wt. % tin, 0.1 wt. % rhenium, 0.2 wt. % platinum and 0.2 wt. % iridium with an alumina carrier material; (5) a catalytic composite comprising a combination of 0.25 wt. % tin, 0.25 wt. % platinum, 0.25 wt. % iridium and 0.25 wt. % rhenium with an alumina carrier material; and, (6) a catalytic composite comprising a combination of 0.2 wt. % tin, 0.2 wt. % rhenium, 0.2 wt. % platinum and 0.2 wt. % iridium with an alumina carrier material. The amounts of the components reported in these examples are, of course, calculated on an elemental basis.

As indicated above, a preferred embodiment of the present invention involves use of a catalytic composite containing an alkali or alkaline earth component. More specifically, this component is selected from the group consisting of the alkali metals — cesium, rubidium, potassium, sodium, and lithium — and of the alkaline earth metals — calcium, strontium, barium, and magnesium. This component may exist within the catalytic composite as a relatively stable compound such as the oxide or sulfide or in combination with one or more of the other components of the composite, or in combination with an alumina carrier material such as in the form of a metal aluminate. Since, as is explained hereinafter, the composite containing the alkali or alkaline earth is always calcined or oxidized in an air atmosphere before use in the conversion of hydrocarbons, the most likely state this component exists in during use in dehydrogenation is in the form of the corresponding metallic oxide. Regardless of what precise form in which it exists in the composite, the amount of this component utilized is preferably selected to provide a composite containing about 0.01 to about 5 wt. % of the alkali or alkaline earth metal, and more preferably, about 0.05 to about 2.5 wt. %. Best results are ordinarily achieved when this component is a compound of lithium or potassium and particularly lithium oxide or potassium oxide.

This alkali or alkaline earth component may be combined with the porous carrier material in any manner known to those skilled in the art such as by impregnation, coprecipitation, physical admixture, ion exchange, etc. However, the preferred procedure involves impregnation of the carrier material either before or after it is calcined and either before, during or after the other components are added to the carrier material. Best results are ordinarily obtained when this component is added after the platinum or palladium, iridium, rhenium and tin components because it serves to neutralize the acid used in the preferred impregnation procedure for incorporation of these components. In fact, it is preferred to add the previously specified metallic components, dry and oxidize the resulting composite, then treat the oxidized composite with steam in order to remove residual acidity, and then add this component by means of an impregnation procedure. Typically, the impregnation of the oxidized composite or of the carrier material is performed by contacting same with a solution of a suitable decomposable compound or salt of the desired alkali or alkaline earth metal. Hence, suitable compounds include the halides, sulfates, nitrates, acetates, carbonates, phosphates, and the like compounds. For example, excellent results are obtained by impregnating the carrier material, after the platinum or palladium, iridium, rhenium and tin components have been combined therewith, with an aqueous solution of lithium nitrate or potassium nitrate. Following the incorporation of this component, the resulting composite is preferably dried and oxidized in an air atmosphere as explained hereinafter.

Regardless of the details of how the components of the catalyst are combined with the porous carrier material, the resulting composite, after one or more of the components are added thereto, generally will be dried at a temperature of about 200° F. to about 600° F. for a period of about 2 to 24 hours or more and finally calcined or oxidized at a temperature of about 600° F. to about 1100° F. in an air atmosphere for a period of about 0.5 to about 10 hours, preferably about 1 to about 5 hours in order to convert substantially all of the metallic components to the corresponding oxide forms. When acidic components are present in any of the reagents used to effect incorporation of any one of the components of the subject composite, it is a good practice to subject the resulting composite to a high temperature treatment with steam, either after or before the calcination step described above, in order to remove as much as possible of the undesired acidic component. For example, when the platinum or palladium component is incorporated by impregnating the carrier material with chloroplatinic acid, it is preferred to subject the resulting composite to a high temperature treatment with steam in order to remove as much as possible of the undesired chloride.

It is essential to subject the resultant oxidized multimetallic catalytic composite to a reduction step with substantially water-free hydrogen prior to its use in the conversion of hydrocarbons. This step is designed to insure a uniform and finely divided dispersion of the metallic components throughout the carrier material and to selectively reduce the platinum or palladium, iridium and rhenium components to the corresponding elemental metallic states, while maintaining the tin component in a positive oxidation state. Preferably, a stream of substantially pure and dry hydrogen (i.e., less than 20 vol. ppm. $H_2O$) is used as the reducing agent in this step. The reducing agent is contacted with the calcined or oxidized composite at reduction conditions, including a temperature of about 800° F. to about 1200° F., a gas hourly space velocity of about 100 to about 10,000 hr.$^{-1}$ and for a period of time of about 0.5 to 10 hours or more, effective to reduce substantially all of the platinum or palladium, iridium and rhenium components to the elemental metallic state while maintaining substantially all of the tin component in a positive oxidation state. This reduction treatment may be performed in situ as part of a start-up sequence if precautions are taken to predry the plant to a substantially water-free state and if a substantially water-free hydrogen stream is used.

The resulting selectively reduced catalytic composite may, in some cases, be beneficially subjected to a presulfiding operation designed to incorporate in the catalytic composite from about 0.05 to about 0.5 wt. % sulfur, calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the selectively reduced catalyst with a sulfiding gas such as a mixture containing a mole ratio of $H_2$ to $H_2S$ of about 10:1 at conditions sufficient to effect the desired incorporation of sulfur, generally including a temperature ranging from about 50° F. up to about 1100° F. or more. This presulfiding step can be performed in situ or ex situ.

According to the method of the present invention, the dehydrogenatable hydrocarbon is contacted with the multimetallic catalytic composite described above in a dehydrogenation zone maintained at dhydrogenation conditions. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system, the hydrocarbon feed stream is preheated by any suitable heating means to the desired reaction temperature and then passed into a dehydrogenation zone containing a fixed bed of the catalyst previously characterized. It is, of course, understood that the dehydrogenation zone may be one or more separate reactors with suitable heating means therebetween to insure that the desired conversion temperature is maintained at the entrance to each reactor. It is also to be noted that the reactants may be contacted with the catalyst bed in either upward, downward, or radial flow fashion with the latter being preferred. In addition, it is to be noted that the reactants may be in the liquid phase, a mixed liquid-vapor phase, or a vapor phase when they contact the catalyst, with best results obtained in the vapor phase.

Although hydrogen is the preferred diluent for use in the subject dehydrogenation method, in some cases other art-recognized diluents may be advantageously utilized such as steam, methane, carbon dioxide, and the like diluents. Hydrogen is preferred because it serves the dual-function of not only lowering the partial pressure of the dehydrogenatable hydrocarbon, but also suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycle hydrogen obtained from the effluent stream from this zone after a suitable hydrogen separation step. When utilizing hydrogen in the instant process, improved results are obtained if water or a water-producing substance (such as an alcohol), ketone, or the like oxygen-containing decomposable organic compound) is added to the dehydrogenation zone in an amount calculated on the basis of equivalent water, corresponding to about 100 to about 4,000 wt. ppm. of the hydrocarbon charge stock, with about 1500 to 2500 wt. ppm. of water giving best results.

Regarding the conditions utilized in the process of the present invention, these are generally selected from the dehydrogenation conditions well known to those skilled in the art for the particular dehydrogenatable hydrocarbon which is charged to the process. More specifically, suitable conversion temperatures are selected from the range of about 700° to about 1250° F. with a value being selected from the lower portion of this range for the more easily dehydrogenated hydrocarbons such as the long chain normal paraffins and from the higher portion of this range for the more difficultly dehydrogenated hydrocarbons such as propane, butane, and the like hydrocarbons. For example, for the dehydrogenation of $C_6$ to $C_{30}$ normal paraffins, best results are ordinarily obtained at a temperature of about 800° to about 950° F. The pressure utilized is ordinarily selected at a value which is as low as possible consistent with the maintenance of catalyst stability and is usually about 0.1 to about 10 atmospheres with best results ordinarily obtained in the range of about 0.5 to about 3 atmospheres. In addition, a liquid hourly space velocity (calculated on the basis of the volume amount, as a liquid, of hydrocarbon charged to the dehydrogenation zone per hour divided by the volume of the catalyst bed utilized) is selected from the range of about 1 to about 40 hr.$^{-1}$, with best results for the dehydrogenation of long chain normal paraffins typically obtained at a relatively high space velocity of about 25 to 35 hr.$^{-1}$.

Regardless of the details concerning the operation of the dehydrogenation step, an effluent stream will be withdrawn therefrom. This effluent will usually contain unconverted dehydrogenatable hydrocarbons, hydrogen, and products of the dehydrogenation reaction. This stream is typically cooled and passed to a hydrogen-separating zone wherein a hydrogen-rich vapor phase is allowed to separate from a hydrocarbon-rich liquid phase. In general, it is usually desired to recover the unreacted dehydrogenatable hydrocarbon from this hydrocarbon-rich liquid phase in order to make the dehydrogenation process economically attractive. This recovery operation can be accomplished in any suitable manner known to the art such as by passing the hydrocarbon-rich liquid phase through a bed of suitable adsorbent material which has the capability to selectively retain the dehydrogenated hydrocarbons contained therein or by contacting same with a solvent having a high selectivity for the dehydrogenated hydrocarbon, or by a suitable fractionation scheme where feasible. In the case where the dehydrogenated hydrocarbon is a mono-olefin, suitable adsorbents having this capability are activated silica gel, activated carbon, activated alumina, various types of specially prepared molecular sieves, and the like adsorbents. In another typical case, the dehydrogenated hydrocarbons can be separated from the unconverted dehydrogenatable hydrocarbons by utilizing the inherent capability of the dehydrogenated hydrocarbons to easily enter into several well known chemical reactions such as alkylation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatable hydrocarbons will typically be recovered from this hydrocarbon separation step and recycled to the dehydrogenation step. Likewise, the hydrogen phase present in the hydrogen-separating zone will be withdrawn therefrom, a portion of it vented from the system in order to remove the net hydrogen make, and the remaining portion is typically recycled through suitable compressing means to the dehydrogenation step in order to provide diluent hydrogen therefor.

In a preferred embodiment of the present invention wherein long chain normal paraffin hydrocarbons are dehydrogenated to the corresponding normal mono-olefins, a preferred mode of operation of this hydrocarbon recovery step involves an alkylation reaction. In this mode, the hydrocarbon-rich liquid phase withdrawn from the hydrogen-separating zone is combined with a stream containing an alkylatable aromatic and the resulting mixture passed to an alkylation zone containing a suitable highly acid catalyst such as an anhydrous solution of hydrogen fluoride. In the alkylation zone the mono-olefins react with alkylatable aromatic while the unconverted normal paraffins remain substantially unchanged. The effluent stream from the alkylation zone can then be easily separated, typically by means of a suitable fractionation system, to allow recovery of the unreacted normal paraffins. The resulting stream of unconverted normal paraffins is then usually recycled to the dehydrogenation step of the present invention.

The following working examples are introduced to illustrate further the novelty, mode of operation, utility, and benefits associated with the dehydrogenation method of the present invention. These Examples are intended to be illustrative rather than restrictive.

These Examples are all performed in a laboratory scale dehydrogenation plant comprising a reactor, a hydrogen separating zone, a heating means, cooling means, pumping means, compressing means, and the like equipment. In this plant, the feed stream containing the dehydrogenatable hydrocarbon is combined with a hydrogen stream and the resultant mixture heated to the desired conversion temperature, which refers herein to the temperature maintained at the inlet to the reactor. The heated mixture is then passed into contact with the catalyst which is maintained as a fixed bed of catalyst particles in the reactor. The pressures reported herein are recorded at the outlet from the reactor. An effluent stream is withdrawn from the reactor, cooled, and passed into the hydrogen-separating zone wherein a hydrogen gas phase separates from a hydrocarbon-rich liquid phase containing dehydrogenated hydrocarbons, unconverted dehydrogenatable hydrocarbons, and a minor amount of side products of the dehydrogenation reaction. a portion of the hydrogen-rich gas phase is recovered as excess recycle gas with the remaining portion being continuously recycled through suitable compressive means to the heating zone as described above. The hydrocarbon-rich liquid phase from the separating zone is withdrawn therefrom and subjected to analysis to determine conversion and selectivity for the desired dehydrogenated hydrocarbon as will be indicated in the Examples. Conversion numbers of the dehydrogenatable hydrocarbon reported herein are all calculated on the basis of disappearance of the dehydrogenatable hydrocarbon and are expressed in mole percent. Similarly, selectivity numbers are reported on the basis of moles of desired hydrocarbon produced per 100 moles of dehydrogenatable hydrocarbon converted.

All of the catalysts utilized in these Examples are prepared according to the following general method with suitable modification in stoichiometry to achieve the compositions reported in each Example. First, an alumina carrier material comprising 1/16 inch spheres is prepared by: forming an alumina hydroxyl chloride sol by dissolving substantially pure aluminum pellets in a hydrochloric acid solution, adding hexamethylenetetramine to the sol, gelling the resulting solution by dropping it into an oil bath to form spherical particles of an alumina hydrogel, aging and washing the resulting particles with an ammoniacal solution and finally drying, calcining, and steaming the aged and washed particles to form spherical particles of gamma-alumina containing substantially less than 0.1 wt. % combined chloride. Additional details as to this method of preparing this alumina carrier material are given in the teachings of U.S. Pat. No. 2,620,314. The resulting gamma-alumina particles are then contacted with an aqueous impregnation solution containing chloroplatinic acid, perrhenic acid, hydrogen chloride, stannous chloride and chloroiridic acid in amounts sufficient to yield a final multimetallic catalytic composite containing the desired amounts of platinum, iridium, rhenium and tin. The hydrochloric acid is utilized in an amount of about 10 wt. % of the alumina particles. The impregnated spheres are then dried at a temperature of about 225° F. for about an hour and thereafter calcined or oxidized in an air atmosphere at a temperature of about 500° F. to about 1000° F. for about 2 to 10 hours effective to convert all of the metallic components to the corresponding oxide forms. In general, it is a good practice to thereafter treat the resulting oxidized particles with an air stream containing about 10 to about 30% steam at a temperature of about 1000° F. for an additional period of about 5 hours in order to reduce the residual combined chloride contained in the catalyst to a value of less than 0.5 wt. % and preferably less than 0.2 wt. %. In the cases shown in the Examples where the catalyst utilized contains an alkali component, this component is added to the oxidized and steam-treated multimetallic catalyst in a separate impregnation step. This second impregnation step involves contacting the oxidized multimetallic catalyst with an aqueous solution of a suitable decomposable salt of the alkali component. For the catalyst utilized in the present Examples, the salt is either lithium nitrate or potassium nitrate. The amount of the salt of the alkali metal utilized is chosen to result in a final catalyst of the desired composition. The resulting alkali impregnated particles are then dried and calcined in an air atmosphere in much the same manner as is described above following the first impregnation step.

In all of the Examples the catalyst is reduced during startup by contacting with dry hydrogen at conditions including a temperature of about 1050° F. for 1 hour at a gas hourly space velocity of about 500 hr.$^{-1}$, effective to reduce the platinum, iridium and rhenium components to the corresponding elemental metals while maintaining the tin component in a positive oxidation state.

EXAMPLE I

The reactor is loaded with 100 cc's of a catalyst containing, on an elemental basis, 0.75 wt. % platinum, 0.5 wt. % rhenium, 0.5 wt. % iridium, 0.5 wt. % tin and less than 0.15 wt. % chloride. The feed stream utilized is commercial grade isobutane containing 99.7 wt. % isobutane and 0.3 wt. % normal butane. The feed stream is contacted with the catalyst at a temperature of 1065° F., a pressure of 10 psig., a liquid hourly space velocity of 4.0 hr.$^{-1}$, and a hydrogen to hydrocarbon mole ratio of 2:1. The dehydrogenation plant is lined-out at these conditions and a 20 hour test period commenced. The hydrocarbon product stream from the plant is continuously analyzed by GLC (gas liquid chromotography) and a high conversion of isobutane is observed with a high selectivity for isobutylene.

EXAMPLE II

The catalyst contains, on an elemental basis, 0.375 wt. % platinum, 0.375 wt. % iridium, 0.375 wt. % rhenium, 0.375 wt. % tin, 0.6 wt. % lithium, and 0.15 wt. % combined chloride. The feed stream is commercial grade normal dodecane. The dehydrogenation reactor is operated at a temperature of 870° F., a pressure of 10 psig., a liquid hourly space velocity of 32 hr.$^{-1}$, and a hydrogen to hydrocarbon mole ratio of 8:1. After a line-out period, a 20 hour test period is performed during which the average conversion of the normal dodecane is maintained at a high level with a selectivity for normal dodecene of about 90%.

EXAMPLE III

The catalyst is the same as utilized in Example II. The feed stream is normal tetradecane. The conditions utilized are a temperature of 840° F., a pressure of 20 psig., a liquid hourly space velocity of 32 hr.$^{-1}$, and a hydrogen to hydrocarbon mole ratio of 8:1. After a line-out period, a 20 hour test shows an average conversion of about 12%, and a selectivity for normal tetradecene of about 90%.

EXAMPLE IV

The catalyst contains, on an elemental basis, 0.375 wt. % platinum, 0.2 wt. % rhenium, 0.375 wt. % iridium, 0.25 wt. % tin and 0.6 wt. % lithium, with combined chloride being less than 0.2 wt. %. The feed stream is substantially pure normal butane. The conditions utilized are a temperature of 950° F., a pressure of 15 psig., a liquid hourly space velocity of 4.0 hr.$^{-1}$ and a hydrogen to hydrocarbon mole ratio of 4:1. After a line-out period, a 20 hour test is performed with an average conversion of the normal butane being about 30% and the selectivity for normal butene is about 80%.

EXAMPLE V

The catalyst contains, on an elemental basis. 0.1 wt. % platinum, 0.1 wt. % iridium, 0.2 wt. % rhenium, 0.25 wt. % tin, 1.5 wt. % potassium, and less than 0.2 wt. % combined chloride. The feed stream is commercial grade ethylbenzene. The conditions utilized are a pressure of 15 psig., a liquid hourly space velocity of 32 hr.$^{-1}$, a temperature of 1050° F., and a hydrogen to hydrocarbon mole ratio of 8:1. During a 20 hour test period, 85% or more of equilibrium conversion of the ethylbenzene is observed. The selectivity for styrene is about 95%.

It is intended to cover by the following claims, all changes and modifications of the above disclosure of the present invention which would be self-evident to a man of ordinary skill in the catalyst-formation art or in the hydrocarbon dehydrogenation art.

I claim as my invention:

1. A method for dehydrogenating a dehydrogenatable hydrocarbon comprising contacting said hydrocarbon, at dehydrogenation conditions, with a catalytic composite comprising a combination of a platinum or palladium component, an iridium component, a rhenium component and a tin component with a porous carrier material in amounts sufficient to result in a composite containing, on an elemental basis, about 0.01 to about 2 wt. % platinum or palladium, about 0.01 to about 2 wt. % iridium, about 0.01 to about 2 wt. % rhenium, and about 0.01 to about 5 wt. % tin, wherein substantially all of the platinum or palladium component, the iridium component and the rhenium component are present in the corresponding elemental metallic state and wherein substantially all of the tin component is present in an oxidation state above that of the elemental metal.

2. A method as defined in claim 1 wherein the dehydrogenatable hydrocarbon is admixed with hydrogen when it contacts the catalytic composite.

3. A method as defined in claim 1 wherein the platinum or palladium component is platinum metal.

4. A method as defined in claim 1 wherein the tin component is tin oxide.

5. A method as defined in claim 1 wherein the porous carrier material is a refractory inorganic oxide.

6. A method as defined in claim 5 wherein the refractory inorganic oxide is gamma- or eta-alumina.

7. A method as defined in claim 1 wherein the dehydrogenatable hydrocarbon is an aliphatic compound containing 2 to 30 carbon atoms per molecule.

8. A method as defined in claim 1 wherein the dehydrogenatable hydrocarbon is a normal paraffin hydrocarbon containing 4 to 30 carbon atoms per molecule.

9. A method as defined in claim 1 wherein the dehydrogenatable hydrocarbon is a naphthene.

10. A method as defined in claim 2 wherein the dehydrogenation conditions include a temperature of 700° to 1250° F., a pressure of 0.1 to 10 atmospheres, an LHSV of 1 to 40 and a hydrogen to hydrocarbon mole ratio of about 1:1 to about 20:1.

11. A method as defined in claim 1 wherein the composite contains, on an elemental basis, about 0.05 to about 1 wt. % platinum or palladium metal, about 0.05 to about 1 wt. % iridium, about 0.05 to about 1 wt. % rhenium, and about 0.05 to about 2 wt. % tin.

12. A method as defined in claim 1 wherein the metals content of the catalytic composite is adjusted so that the atomic ratio of tin to platinum or palladium is about 0.1:1 to about 3:1, the atomic ratio of rhenium to platinum or palladium is about 0.1:1 to about 3:1 and the atomic ratio of iridium to platinum or palladium is about 0.1:1 to about 2:1.

* * * * *